(12) United States Patent
Stivers

(10) Patent No.: US 11,678,857 B2
(45) Date of Patent: Jun. 20, 2023

(54) BREAKAWAY STETHOSCOPE SYSTEM AND METHOD

(71) Applicant: PTM, LLC, Bellevue, WA (US)

(72) Inventor: Joshua Allen Stivers, Puyallup, WA (US)

(*) Notice: Subject to any disclaimer, the term of this patent is extended or adjusted under 35 U.S.C. 154(b) by 0 days.

(21) Appl. No.: 17/878,651

(22) Filed: Aug. 1, 2022

(65) Prior Publication Data

US 2022/0361838 A1 Nov. 17, 2022

Related U.S. Application Data

(63) Continuation of application No. 15/941,806, filed on Mar. 30, 2018, now Pat. No. 11,432,791.

(51) Int. Cl.
 *A61B 7/02* (2006.01)
 *G10K 11/18* (2006.01)

(52) U.S. Cl.
 CPC ........ *A61B 7/02* (2013.01); *A61B 2560/0443* (2013.01); *G10K 11/18* (2013.01)

(58) Field of Classification Search
 CPC .................................. A61B 7/02; G10K 11/18
 USPC ......................................................... 181/131
 See application file for complete search history.

(56) References Cited

U.S. PATENT DOCUMENTS

| 977,503 A | 12/1910 | Baylis |
| 1,817,489 A | 8/1931 | Jones |
| 2,209,164 A | 7/1940 | Kerr |
| 2,515,471 A | 7/1950 | Ratzan |
| 2,807,328 A | 9/1957 | Gould |
| 3,169,600 A * | 2/1965 | Thomas ................. H04R 1/345 181/135 |
| 3,621,845 A | 11/1971 | Oates |
| 4,064,965 A | 12/1977 | Brown |
| 4,299,303 A | 11/1981 | Clark |
| 4,497,124 A * | 2/1985 | Olive ........................ G09F 3/00 181/131 |
| 4,633,971 A | 1/1987 | Robbins |
| 4,997,055 A | 3/1991 | Grady |
| 5,650,598 A | 7/1997 | Abelson |
| 5,798,489 A | 8/1998 | Gillio |
| 5,844,995 A | 12/1998 | Williams |
| 5,945,641 A | 8/1999 | Shieh |
| 5,959,261 A | 9/1999 | Abelson |
| D432,237 S | 10/2000 | Shick |
| 6,308,798 B1 | 10/2001 | Rashman et al. |
| 6,656,128 B1 | 12/2003 | Linck et al. |
| 6,691,821 B2 | 2/2004 | Oster et al. |
| 7,516,814 B1 | 4/2009 | Berk et al. |

(Continued)

*Primary Examiner* — Jeremy A Luks

(57) ABSTRACT

A breakaway stethoscope includes a chest piece, a headset, a tube, and a coupler. The chest piece captures sounds generated inside a person's body when the chest piece is positioned adjacent the person's body. The headset directs the sounds captured by the chest piece toward a person's ear when the headset is positioned on an ear of the person. The tube connects the chest piece to the headset and conveys the sounds captured by the chest piece toward the headset. The tube has a length and includes a first portion connected to the chest piece and a second portion connected to the headset. The coupler releasably connects the tube's first portion to the tube's second portion and releases one of the tube's portions when the tube experiences a force that urges at least one of the tube's portions to move away from the coupler.

14 Claims, 3 Drawing Sheets

(56) References Cited

U.S. PATENT DOCUMENTS

| | | |
|---|---|---|
| 7,841,445 B2 | 11/2010 | Berk et al. |
| 9,486,180 B2 | 11/2016 | Ting |
| 2004/0226771 A1 | 11/2004 | Werblud |
| 2011/0048841 A1 | 3/2011 | Hasbun |
| 2011/0088964 A1 | 4/2011 | MacMackin |
| 2012/0190303 A1 | 7/2012 | Wong |
| 2019/0150880 A1 | 5/2019 | Campbell et al. |
| 2019/0274656 A1 | 9/2019 | Pande et al. |

* cited by examiner

BREAKAWAY STETHOSCOPE SYSTEM AND METHOD

CROSS REFERENCE TO RELATED APPLICATIONS

This application claims priority to U.S. Non Provisional application Ser. No. 15/941,806 filed on Mar. 30, 2018 which is incorporated in its entirety

BACKGROUND

Medical staff, such as doctors, nurses and technicians, are often required to deal with unruly and/or aggressive patients that may become violent and cause injury to themselves or others. Medical staff also often carry and wear a stethoscope while working and tend to rest the stethoscope around the neck and on the shoulders when not in use. Unfortunately, violent patients may see that as an opportunity to harm the doctor, nurse or technician by grabbing the stethoscope that is resting on the wearer's neck and strangle or injure the wearer and in some cases cause death. Thus, there is a need for a breakaway stethoscope that will separate into two or more pieces when forcefully pulled on or forcefully wrapped around a doctor's, nurse's, or technician's throat to prevent injury or death to the doctor, nurse or technician.

SUMMARY

In one aspect of the invention, a breakaway stethoscope includes a chest piece, a headset, a tube, and a coupler. The chest piece captures sounds generated inside a person's body when the chest piece is positioned adjacent the person's body. The headset directs the sounds captured by the chest piece toward a person's ear when the headset is positioned on an ear of the person. The tube connects the chest piece to the headset and conveys the sounds captured by the chest piece toward the headset. The tube has a length and includes a first portion connected to the chest piece and a second portion connected to the headset. The coupler releasably connects the tube's first portion to the tube's second portion and releases one of the tube's portions when the tube experiences a force that urges at least one of the tube's portions to move away from the coupler.

By releasing one of the tube's portions when the tube experiences a force that stretches the tube in length, the stethoscope's coupler allows the portion of the tube that experiences the force to break away from the other portion of the tube, much like a lizzard's tail breaks away from the lizzard's body to allow the lizard to escape capture. This in turn, protects a doctor, nurse or technician using the stethoscope to listen to sounds generated inside a patient or another person's body from being strangled or physically coerced into doing something that the doctor, nurse or technician does not want to do. The doctor, nurse or technician can also protect their ears if the tube is pulled by the patient or the other person by simply grabbing the stethoscope's headset and/or portion of the tube that is connected to the stethoscope's headset and preventing the earpieces of the headset from damaging his/her ears.

In another aspect of the invention, a method for releasably connecting a first portion of a tube of a stethoscope to a second portion of the stethoscope's tube, includes: a) holding a first portion of a stethoscope's tube with a coupler; b) holding a second portion of the stethoscope's tube with the coupler; and c) releasing the coupler's hold on at least one of the stethoscope's first and second portions in response to a force exerted on the stethoscope's tube that urges at least one of the tube's portions to move away from coupler.

DETAILED DESCRIPTION

Figure 1:
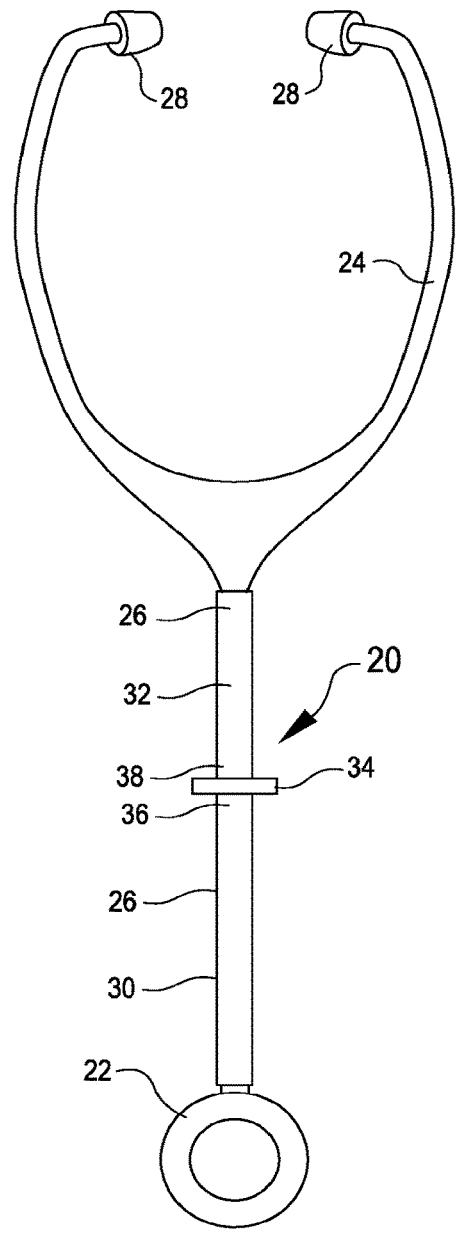
FIG. 1 shows a view of a breakaway stethoscope with the stethoscope's sections connected to each other, according to an embodiment of the invention.
Figure 2:
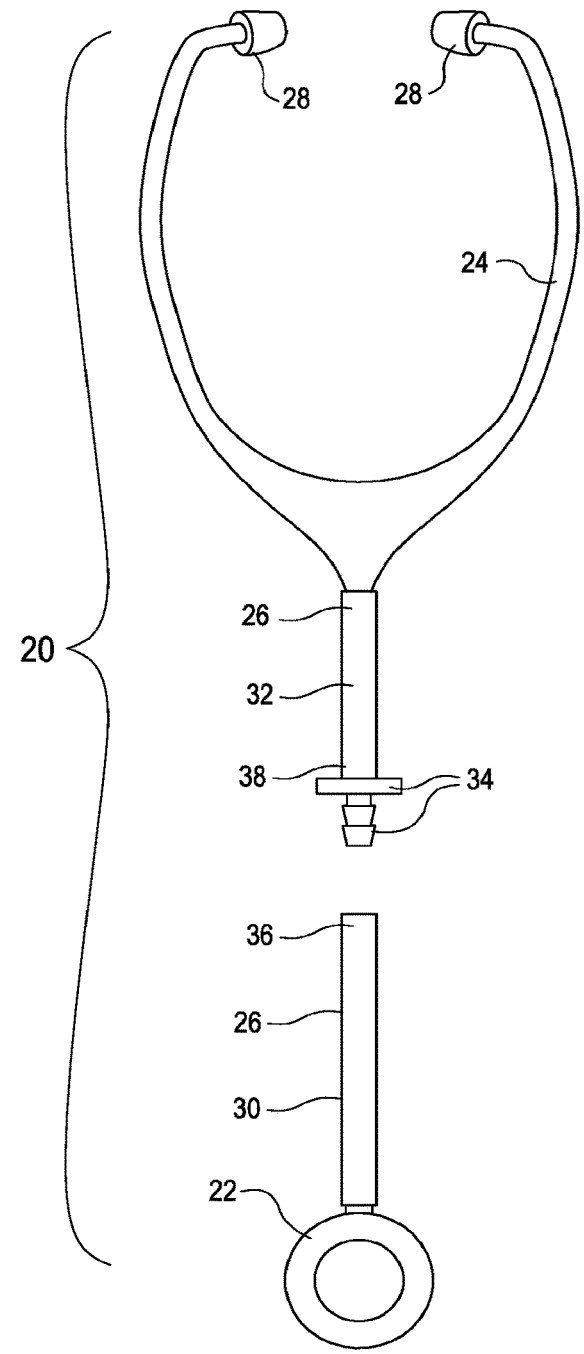
FIG. 2 shows the breakaway stethoscope in FIG. 1 with the stethoscope's sections separated from each other, according to an embodiment of the invention.

Each of FIGS. 1 and 2 shows a view of a breakaway stethoscope 20, according to an embodiment of the invention. FIG. 1 shows the stethoscope 20 whole and ready for use, and FIG. 2 shows the stethoscope 20 in two pieces after one of the pieces has broken away from the other. The stethoscope 20 includes a chest piece 22 that captures sounds generated inside a person's body when the chest piece 22 is placed on the person's body. For example, if a doctor, nurse or technician wants to listen to a patient's breathing or beating heart, then the doctor or nurse would position and hold the chest piece 22 on the person's chest adjacent the person's lungs or heart. The chest piece 22 would then capture the sounds of air flowing into and out of the patient's lungs or the sounds of the patient's heart beating. To direct and convey toward the doctor, nurse or technician's ear the sounds captured by the chest piece 22, the stethoscope 20 also includes a headset 24 and a tube 26 that connects the headset 24 to the chest piece 22. The headset 26 includes an earpiece 28 (here two) each of which contacts a respective one of the doctor, nurse or technician's ears when the doctor, nurse or technician uses the stethoscope 20 to listen to sounds generated inside a person's body. The tube 24 includes a first portion 30 connected to the chest piece 22, a second portion 32 connected to the headset 24, and a length that is equal to the sum of the lengths of each of the portions 30 and 32. The stethoscope 20 also includes a coupler 34 (discussed in greater detail in conjunction with FIGS. 3 and 4) that releasably connects the tube's first portion 30 to the tube's second portion 32 and releases one of the tube's portions 30 and 32 when the tube 26 experiences a force that urges at least one of the tube's portions 30 and 32 to move away from the coupler 34. In other words, when the tube 26 experiences a force that urges the tube 26 to stretch beyond its length, the coupler 34 releases one or both of the tube's portions 30 and 32 (see FIG. 2).

By releasing one of the tube's portions 30 and 32 when the tube 26 experiences a force that stretches the tube 26 in length, the stethoscope's coupler 34 allows the portion 30 and/or 32 of the tube 26 that experiences the force to break away from the other portion 32 and/or 30 of the tube 26. This in turn, protects a doctor, nurse or technician using the stethoscope 20 from being strangled or physically coerced into doing something that the doctor, nurse or technician does not want to do. The doctor, nurse, or technician can also protect their ears if the tube 26 is pulled by the patient or the other person by simply grabbing the stethoscope's headset 24 and/or portion 32 of the tube 26 that is connected to the stethoscope's headset 24 and preventing the earpieces 28 of the headset 24 from damaging his/her ears.

Figure 3:
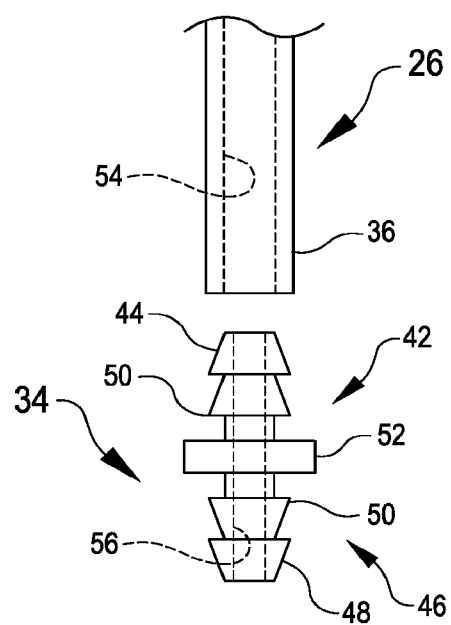
FIG. 3 shows an exploded view of a coupler and a portion of a tube of the breakaway stethoscope shown in FIGS. 1 and 2, according to an embodiment of the invention.
Figure 4:
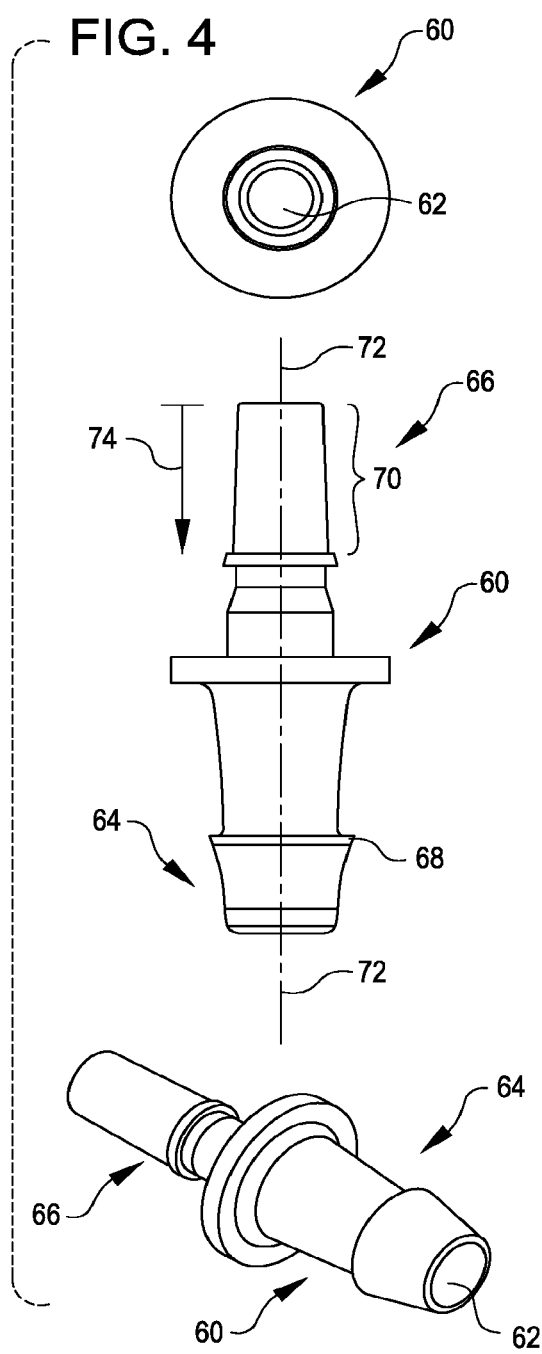
FIG. 4 shows three views of a stethoscope's coupler, according to another embodiment of the invention.

As discussed in greater detail in conjunction with FIGS. 3 and 4, the coupler 34 may be configured as desired to release one or both of the portions 30 and 32 when the tube 26 experiences any desired force. For example, in this and other embodiments the coupler 34 may be configured to release one or both of the portions 30 and 32 when the force experienced by the tube 26 reaches about four pounds. With a four-pound separation force, the coupler 34 can easily keep the chest piece 22 coupled to the headset 24 and yet quickly release the first and/or second portions 30 and 32 if someone grasps the chest piece 22 and tries to pull it away from the headset 24 while a doctor, nurse or technician is using the stethoscope 20. The four-pound separation force also allows the coupler 34 to quickly release the first and/or second portions 30 and 32 if someone grasps one of the tube's portions 30 or 32 and attempts to forcefully wrap the tube 26 around a doctor, nurse or technician's neck. In other embodiments, the coupler 34 may be configured to release one or both of the portions 30 and 32 when the force experienced by the tube 26 reaches about 11 pounds. With an eleven-pound separation force, the coupler 34 can continue to hold both of the tube's portions 30 and 32 if the stethoscope 20 gets snagged by a corner of a desk or some other protrusion while being carried in a doctor, nurse or technician's pocket, and thus will be easier to recognize when the stethoscope 20 gets pulled out of the doctor, nurse or technician's pocket.

Still referring to FIGS. 1 and 2, the chest piece 22 and headset 24 may be configured as desired to capture, direct and convey any desired sounds. For example, in this and other embodiments the chest piece 22 is a conventional chest piece 22 designed to capture the sounds that a heart makes while it beats. In other embodiments, the chest piece 22 may include a tunable diaphragm to allow one to focus on a range of frequencies of the sounds that one wants the chest piece 22 to capture. For example, a diaphragm whose tension is low more easily captures sounds having a low frequency, such as a murmur in the beating of a heart, while a diaphragm whose tension is high more easily captures sounds having a high frequency, such as the wheezing sound of a lung that is partially filled with a liquid. In this and other embodiments, the headset 24 is a conventional headset made of aluminum.

Still referring to FIGS. 1 and 2, the tube 26 may be configured as desired to convey toward the headset 24 the sounds captured by the chest piece 22. For example, in this and other embodiments the tube 26 includes a single lumen that is approximately 0.2 inches in diameter and is made of latex rubber. More specifically, the first and second portions 30 and 32 of the tube 26 are flexible along their entire lengths. In other embodiments, the tube 26 includes dual lumens that run parallel to each other the entire length of the tube 26. In yet other embodiments, the tube 26 may only be flexible in the regions of the first and second portions 30 and 32 that the coupler 34 holds—more specifically, the first end 36 of the tube's first portion 30 and the first end 38 of the tube's second portion 32.

Other embodiments are possible. For example, the stethoscope 20 may include two or more couplers 34 that connect three or more portions of the tube 26 together. Additional couplers 34 may be desirable to provide more breakaway locations to the stethoscope 20, and thus make it harder for someone to circumvent a single breakaway location by grabbing the tube 26 where the coupler 34 is located.

FIG. 3 shows an exploded view of the coupler 34 and a portion of the tube 26 of the stethoscope 20 shown in FIGS. 1 and 2, according to an embodiment of the invention. The coupler 34 may be configured as desired to release one or both of the portions 30 and 32 when the tube 26 experiences any desired force. For example, in this and other embodiments the coupler 34 includes a first section 42 having a first end 44 and a second section 46 having a first end 48, and is designed to allow the first end 36 of the tube's first portion 30 (FIGS. 1 and 2) to slide off of the first section 42 when the tube 26 experiences a force of about four pounds that urges the first end 36 to move relative to the coupler's first section 42. Similarly, the coupler 34 is designed to also allow the first end 38 (FIGS. 1 and 2) of the tube's second portion 32 (FIGS. 1 and 2) to slide off of the second section 46 when the first end 38 experiences a force of about four pounds that urges the first end 38 to move relative to the coupler's second section 46. In reality, both first ends 36 and 38 of the tube 26 will rarely slide off of their respective coupler sections 42 and 46, simultaneously. Instead, one of the first ends 36 and 38 will begin to slide off of its respective section 42 or 46, and thus reduce the force experienced by the other first end 38 or 36 of the tube 26. The sliding first end 36 or 38 will then continue to slide relative to its respective coupler section 42 or 46 until the coupler 34 no longer holds the first end 36 or 38, at which point the first and second portions 30 and 32 of the tube 26 will be separated or broken away from each other.

The coupler's sections 42 and 46 may be configured as desired to provide the desired friction to resist the movement of either of the first ends 36 and 38 relative to their respective coupler sections 42 and 46. For example, in this and other embodiments each of the coupler's sections 42 and 46 includes a barb 50 that is configured to allow the first end 36 or 38 to move toward the center 52 of the coupler 34 in response to a force that is less than four pounds, but to not allow the first end 36 or 38 to move away from the center 52 in response to a force that is less than four pounds. More specifically, the larger diameter of the barb 50 is approximately 0.24 inches in diameter and locally stretches the inside surface of the first end's lumen 54, which is about 0.2 inches in diameter. And, the smaller diameter of the barb 50 is approximately 0.2 inches in diameter. To provide more friction resistance against the first end 36 or 38 moving away from the coupler's center 52, the larger diameter of the barb 50 may be greater than 0.24 inches, and/or the diameter of the first end's lumen 54 may be less than 0.2 inches. In addition, material, such as an adhesive, may be applied to the surface of the barb 50 that increases the coefficient of friction between the barb 50 and the inside surface of the lumen 54 that the barb 50 contacts. Also, more than two barbs 50 may be used to contact the inside surface of the first end's lumen 54. Likewise, to provide less friction resistance against the first end 36 or 38 moving away from the coupler's center 52, the larger diameter of the barb 50 may be less than 0.24 inches, and/or the diameter of the first end's lumen 54 may be greater than 0.2 inches. In addition, material, such as a lubricant, may be applied to the surface of the barb 50 that decreases the coefficient of friction between the barb 50 and the inside surface of the lumen 54 that the barb 50 contacts. Also, less than two barbs 50 may be used to contact the inside surface of the first end's lumen 54.

Still referring to FIG. 3, the coupler 34 may be made of any desired material. For example, in this and other embodiments, the coupler 34 is made of brass, and includes a lumen 56 to convey the sounds captured by the chest piece 22, from the first portion 30 of the tube 26 to the second portion 32 of the tube 26. In other embodiments, the coupler 34 may be made of plastic and include dual lumens extending parallel to each other through the coupler 34.

Other embodiments of the coupler 34 are possible. For example, the coupler 34 may include a receiver whose inside surface contacts the outside surface of the first end 36 and frictionally resists movement of the first end 36 away from the coupler 34. In such embodiments, the coupler's receiver may release the first end 36 when the first end experiences a force that urges the first end to move away from receiver, by reducing the first end's outside diameter and thus reducing the friction resistance between the receiver and the first end 36. If the first end 36 is flexible, then the first end's outside diameter will decrease as the first end's material is stretched lengthwise. This reduction in the diameter will cause the contact force between the receiver and the first end to decrease and thus decrease the friction resistance between the two. For another example, the coupler 34 may include a breakaway portion whose material and cross-sectional area is designed such that the material will fracture when the force transmitted through the material reaches the desired breakaway force for the stethoscope, such as four pounds.

FIG. 4 shows three views of a stethoscope's coupler 60, according to another embodiment of the invention. The three views include a perspective view, a side view, and a front view that allows on to look through the coupler's lumen 62. The coupler 60 is similar to the coupler 34 in that it releasably connects a stethoscope tube's first and second portions together and releases one of the portions when the tube 26 experiences a force that urges the stethoscope's chest piece to move away from the stethoscope's headset a distance that is greater than the tube's length. The difference between the coupler 34 and the coupler 60 is that the coupler 60 includes a first section 64 that does not allow an end of a tube 26 that surrounds it to slide off when the tube 26 experiences a breakaway force, and a second section 66 that does allow an end of a tube 26 to slide off when the tube 26 experiences a breakaway force. More specifically, the first section 64 includes a barb 68 that is configured to contact the inside surface of the tube's lumen and generate a friction force between the barb 68 and the lumen's inside surface that does not allow the tube 26 to slide over the barb 68 and off of the first section 64. The second section 66 includes a surface 70 that has a Luer taper, that is, the distance of the surface 70 from the axis 72 increases by 6% as the surface 70 extends in the direction indicated by the reference number 74. With the Luer taper, the breakaway force required to separate the tube 26 from the coupler's second section can be finely tuned because the total friction force that resists the breakaway force is directly proportional to the total surface area of the surface 70. To increase the breakaway force, one may extend the length of the surface 70 in the direction indicated by the arrow 74, and to decrease the breakaway force one may shorten the length of the surface 70.

Figure 5:
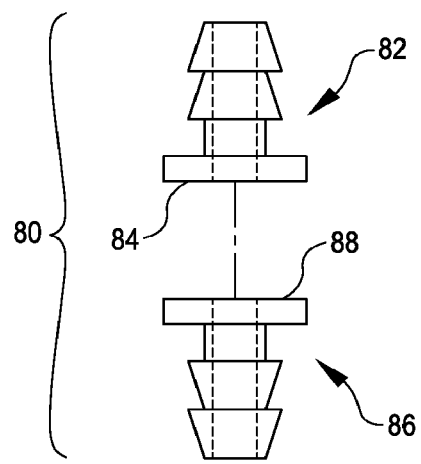
FIG. 5 shows a view of a stethoscope's coupler, according to yet another embodiment of the invention.

FIG. 5 shows a view of a stethoscope's coupler 80, according to yet another embodiment of the invention. The coupler 80 is similar to the coupler 34 in that it releasably connects a stethoscope tube's first and second portions together and releases one of the portions when the tube 26 experiences a force that urges the stethoscope's chest piece to move away from the stethoscope's headset a distance that is greater than the tube's length. The difference between the coupler 34 and the coupler 80 is that the coupler 80 breaks into two sections when the tube experiences the breakaway force. More specifically, the coupler 80 includes a first section 82 that includes a first magnet 84, and a second section 86 that includes a second, complimentary magnet 88. The magnets 86 and 68 are configured to provide enough magnetic attraction to each other so that a force that is less than the desired breakaway force (here four pounds) will not separate the magnets 86 and 88; but a force that meets or exceeds the breakaway force will separate the magnets 86 and 88. Because the magnets 86 and 88 provide the breakaway mechanism for the coupler 80, the first and second sections of the coupler 80 are configured to hold the ends of the tube when the force experienced by the tube exceeds the breakaway force. The preceding discussion is presented to enable a person skilled in the art to make and use the invention. Various modifications to the embodiments will be readily apparent to those skilled in the art, and the generic principles herein may be applied to other embodiments and applications without departing from the spirit and scope of the present invention. Thus, the present invention is not intended to be limited to the embodiments shown, but is to be accorded the widest scope consistent with the principles and features disclosed herein.

The corresponding structures, materials, acts, and equivalents of any means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention.

The embodiments were chosen and described in order to best explain the principles of the invention and the practical application, and to enable others of ordinary skill in the art to understand the invention for various embodiments with various modifications as are suited to the particular use contemplated. The present invention, according to one or more embodiments described in the present description, may be practiced with modification and alteration within the spirit and scope of the appended claims. Thus, the description is to be regarded as illustrative instead of restrictive of the present invention.

What is claimed is:

1. A breakaway stethoscope comprising:
   a chest piece that captures sounds generated inside a person's body when the chest piece is positioned adjacent to the person's body;
   a headset that directs the sounds captured by the chest piece; and
   a coupler that is symmetrically vertically and horizontally and releasably connects a first tube connected to the chest piece and a second tube connected to the headset and releases the first tube or the second tube when the first tube or the second tube experiences a predetermined force, the coupler having a first section and a second section on opposite ends of the coupler, the first section and the second section each having one or more barbs wherein the first tube and the second tube are positioned over the one or more barbs wherein the first section and the second section are separated by a disc at a center of the coupler wherein when the first tube and the second tube are connected to the coupler they directly rest against the disc and cover the first section and the second section.

2. The breakaway stethoscope of claim 1 wherein the first section and the second section have two barbs each.

3. The breakaway stethoscope of claim 1 wherein adhesive is attached to the one or more barbs.

4. The breakaway stethoscope of claim 1 wherein the one or more barbs have an area of smaller diameter and an area of larger diameter, the area of the larger diameter is positioned closer to the center of the coupler.

5. The breakaway stethoscope of claim 4 wherein the larger diameter is 0.24 inches and the smaller diameter is 0.2 inches.

6. The breakaway stethoscope of claim 1 further comprising a second coupler that releasably connects a third tube to the second tube or the first tube.

7. A breakaway stethoscope comprising:
a vertically and horizontally symmetrical coupler that releasably connects a first tube connected to a chest piece and a second tube connected to a headset and releases the first tube or the second tube when the first tube or the second tube experiences a predetermined force, the coupler having a first section and a second section on opposite ends of the coupler, the first section and the second section each having one or more barbs positioned a distance on opposite sides of a disc at a center of the coupler, wherein the disc if of larger diameter than the one or more barbs.

8. The breakaway stethoscope of claim 7 wherein the first section and the second section have two barbs each.

9. The breakaway stethoscope of claim 7 wherein adhesive is attached to the one or more barbs.

10. The breakaway stethoscope of claim 7 wherein the one or more barbs have an area of smaller diameter and an area of larger diameter, the area of the larger diameter is positioned closer to the center of the coupler.

11. The breakaway stethoscope of claim 10 wherein the larger diameter is 0.24 inches and the smaller diameter is 0.2 inches.

12. The breakaway stethoscope of claim 7 further comprising a second coupler that releasably connects a third tube to the second tube or the first tube.

13. A breakaway stethoscope comprising:
a coupler that releasably connects a single first tube connected to a chest piece and a single second tube connected to a headset and releases the single first tube or the single second tube when the single first tube or the single second tube experiences a predetermined force, the coupler having a plurality of barbs for the single first tube and the single second tube to be positioned over the plurality of barbs, wherein a disc is at a center of the coupler wherein when the single first tube and the single second tube are connected to the coupler they directly rest against the disc on opposing sides.

14. The breakaway stethoscope of claim 13 wherein the plurality of barbs have an area of smaller diameter and an area of larger diameter, the area of the larger diameter is positioned closer to the center of the coupler.

* * * * *